(12) United States Patent
Ingram et al.

(10) Patent No.: US 10,214,482 B2
(45) Date of Patent: Feb. 26, 2019

(54) DIAMINE HAVING TERT-ALKYLAMINO GROUP AND PRIMARY AMINO GROUP FOR USE IN GAS SCRUBBING

(71) Applicant: BASF SE, Ludwigshafen (DE)

(72) Inventors: Thomas Ingram, Mannheim (DE); Marion Da Silva, Mannheim (DE); Georg Sieder, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/506,472

(22) PCT Filed: Aug. 20, 2015

(86) PCT No.: PCT/EP2015/069164
§ 371 (c)(1),
(2) Date: Feb. 24, 2017

(87) PCT Pub. No.: WO2016/030277
PCT Pub. Date: Mar. 3, 2016

(65) Prior Publication Data
US 2018/0222847 A1    Aug. 9, 2018

(30) Foreign Application Priority Data
Aug. 25, 2014  (EP) .................................... 14182096

(51) Int. Cl.
*B01D 53/14* (2006.01)
*B01D 53/52* (2006.01)
(Continued)

(52) U.S. Cl.
CPC ........ *C07C 217/42* (2013.01); *B01D 53/1425* (2013.01); *B01D 53/1462* (2013.01);
(Continued)

(58) Field of Classification Search
None
See application file for complete search history.

(56) References Cited

U.S. PATENT DOCUMENTS

| 2,845,408 | A | * | 7/1958 | Melamed | ................. | B01J 23/94 |
| | | | | | | 252/77 |
| 4,112,050 | A | | 9/1978 | Sartori et al. | | |

(Continued)

FOREIGN PATENT DOCUMENTS

| CA | 1 214 024 A | 11/1986 |
| CA | 1290553 C | 10/1991 |

(Continued)

OTHER PUBLICATIONS

International Search Report dated Oct. 27, 2015 in PCT/EP2015/069164.

*Primary Examiner* — Daniel Berns
(74) *Attorney, Agent, or Firm* — Oblon, McClelland, Maier & Neustadt, L.L.P.

(57) ABSTRACT

A compound of the general formula (I)

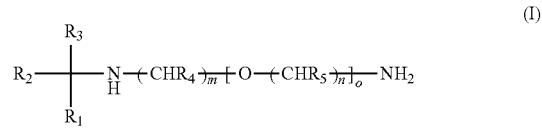

in which $R_1$, $R_2$ and $R_3$ are independently selected from $C_{1-4}$-alkyl and $C_{1-4}$-hydroxyalkyl; each $R_4$ is independently selected from hydrogen, $C_{1-4}$-alkyl and $C_{1-4}$-hydroxyalkyl; each $R_5$ is independently selected from hydrogen, $C_{1-4}$-alkyl and $C_{1-4}$-hydroxyalkyl; m is 2, 3, 4 or 5; n is 2, 3, 4 or 5; and o is an integer from 0 to 10. A preferred compound of the (Continued)

formula (I) is 2-(2-tert-butylaminoethoxy)ethylamine. Absorbents comprising a compound of the formula (I) have rapid absorption of carbon dioxide from fluid streams and are also suitable for processes for the simultaneous removal of $H_2S$ and $CO_2$, where given $H_2S$ limits have to be observed but complete removal of $CO_2$ is not required.

14 Claims, 4 Drawing Sheets

(51) Int. Cl.
| | |
|---|---|
| *B01D 53/62* | (2006.01) |
| *B01D 53/78* | (2006.01) |
| *B01D 53/96* | (2006.01) |
| *C07C 217/42* | (2006.01) |
| *B01J 31/24* | (2006.01) |
| *C07C 217/08* | (2006.01) |
| *C10L 3/10* | (2006.01) |

(52) U.S. Cl.
CPC .......... *B01D 53/1493* (2013.01); *B01J 31/24* (2013.01); *C07C 217/08* (2013.01); *C10L 3/103* (2013.01); *C10L 3/104* (2013.01); *B01D 2252/2025* (2013.01); *B01D 2252/20421* (2013.01); *B01D 2252/20426* (2013.01); *B01D 2252/20431* (2013.01); *B01D 2252/20442* (2013.01); *B01D 2252/20447* (2013.01); *B01D 2252/20452* (2013.01); *B01D 2252/20489* (2013.01); *B01D 2252/504* (2013.01); *B01D 2256/245* (2013.01); *B01D 2257/302* (2013.01); *B01D 2257/304* (2013.01); *B01D 2257/306* (2013.01); *B01D 2257/308* (2013.01); *B01D 2257/504* (2013.01); *B01D 2258/025* (2013.01); *B01D 2258/0233* (2013.01); *B01D 2258/0266* (2013.01); *B01D 2258/0283* (2013.01); *B01D 2258/05* (2013.01); *C10L 2290/06* (2013.01); *C10L 2290/12* (2013.01); *C10L 2290/48* (2013.01); *C10L 2290/541* (2013.01); *C10L 2290/545* (2013.01); *Y02C 10/06* (2013.01); *Y02P 20/152* (2015.11)

(56) References Cited

U.S. PATENT DOCUMENTS

| | | | |
|---|---|---|---|
| 4,112,051 | A | 9/1978 | Sartori et al. |
| 4,112,052 | A | 9/1978 | Sartori et al. |
| 4,336,233 | A | 6/1982 | Appl et al. |
| 4,471,138 | A | 9/1984 | Stogryn |
| 4,537,753 | A | 8/1985 | Wagner et al. |
| 4,553,984 | A | 11/1985 | Volkamer et al. |
| 4,894,178 | A | 1/1990 | Ho et al. |
| 4,997,630 | A | 3/1991 | Wagner et al. |
| 2009/0264651 | A1 | 10/2009 | Daly |
| 2009/0264675 | A1 | 10/2009 | Daly |
| 2013/0243676 | A1 | 9/2013 | Siskin et al. |

FOREIGN PATENT DOCUMENTS

| | | |
|---|---|---|
| CA | 1295810 C | 2/1992 |
| DE | 26 28 376 A1 | 1/1977 |
| EP | 0 121 109 A2 | 10/1984 |
| EP | 0 159 495 A2 | 10/1985 |
| EP | 0 190 434 A2 | 8/1986 |
| EP | 0 202 600 A2 | 11/1986 |
| EP | 0359991 | 3/1990 |
| WO | WO 00/00271 A1 | 1/2000 |
| WO | WO 2009/137765 A1 | 11/2009 |
| WO | WO 2013/138443 A1 | 9/2013 |

\* cited by examiner

DIAMINE HAVING TERT-ALKYLAMINO GROUP AND PRIMARY AMINO GROUP FOR USE IN GAS SCRUBBING

The present invention relates to particular diamine compounds, to absorbents comprising these compounds, to the use of these absorbents for removing carbon dioxide and/or hydrogen sulfide from fluid streams, and to processes for removing carbon dioxide and/or hydrogen sulfide from fluid streams.

The removal of acid gases, for example $CO_2$, $H_2S$, $SO_2$, $CS_2$, HCN, COS or mercaptans, from fluid streams such as natural gas, refinery gas or synthesis gas is important for various reasons. $CO_2$ in conjunction with water, which is frequently entrained in the fluid streams, can form acids, which lead to corrosion in pipes and valves. Carbon dioxide has to be removed from natural gas among other substances to such an extent that the calorific value of the gas does not fall below the desired value. For further processing in a natural gas liquefaction plant (LNG=liquefied natural gas), $CO_2$, in contrast, has to be removed completely.

The content of sulfur compounds in natural gas has to be reduced directly at the natural gas source through suitable treatment measures, since the sulfur compounds form acids having corrosive action in the water frequently entrained by the natural gas. For the transport of the natural gas in a pipeline or further processing in a natural gas liquefaction plant (LNG=liquefied natural gas), given limits for the sulfur-containing impurities therefore have to be observed. In addition, numerous sulfur compounds are malodorous and toxic even at low concentrations.

Acid gases are removed by using scrubbing operations with aqueous solutions of inorganic or organic bases. When acid gases are dissolved in the absorbent, ions form with the bases. The absorption medium can be regenerated by decompression to a lower pressure and/or by stripping, in which case the ionic species react in reverse to form acid gases and/or are stripped out by means of steam. After the regeneration process, the absorbent can be reused.

High $CO_2$ absorption rates are achieved through the use of absorbents having a high $CO_2$ affinity, such as primary and secondary alkanolamines. High $CO_2$ affinity requires that the $CO_2$ absorption proceeds with high exothermicity. However, absorbents of this kind, because of the high magnitude of the absorption reaction enthalpy, generally also entail a relatively high energy consumption in the regeneration.

Highly sterically hindered secondary amines, such as 2-(2-tert-butylaminoethoxy)ethanol, and tertiary amines, such as methyldiethanolamine (MDEA), exhibit kinetic selectivity for $H_2S$ over $CO_2$. These amines do not react directly with $CO_2$; instead, $CO_2$ is reacted in a slow reaction with the amine and with water to give bicarbonate—in contrast, $H_2S$ reacts immediately in aqueous amine solutions. These amines are therefore especially suitable for selective removal of $H_2S$ from gas mixtures comprising $CO_2$ and $H_2S$.

Sterically unhindered primary or secondary amines, for example piperazine, can accelerate the $CO_2$ absorption of tertiary amines as promoters through intermediate formation of a carbamate structure. In this direct reaction of the amine with carbon dioxide, the absorption rate is high, but on the other hand only one $CO_2$ molecule can be absorbed by two amine molecules. For instance, U.S. Pat. No. 4,336,233 discloses a process for removing $CO_2$ and/or $H_2S$ from gases by means of an aqueous absorbent comprising MDEA and piperazine. The use of piperazine as $CO_2$ promoter enables a $CO_2$ absorption rate many times higher compared to systems without a promoter.

US 2013/0243676 describes a process for absorption of $H_2S$ and $CO_2$ from a gas mixture with an absorbent comprising a highly sterically hindered etheramine triethylene glycol alcohol or derivatives thereof and a liquid amine.

U.S. Pat. No. 4,471,138 showed that highly sterically hindered secondary amines such as 2-(2-tert-butylaminoethoxy)ethanol (TBAEE), even in combination with further amines such as methyldiethanolamine (MDEA), have a much higher $H_2S$ selectivity than MDEA. Amines which are referred to as highly sterically hindered are those wherein the nitrogen atom therein is bonded to one or more extensive groups and which have a cumulative steric parameter (Taft constant) $E_s$ of more than 1.75.

It is an object of the invention to specify compounds which have rapid absorption of carbon dioxide from fluid streams, without any significant increase in the required regeneration energy compared to absorbents based on secondary and tertiary amines. The absorbent should also be suitable for the simultaneous removal of $H_2S$ and $CO_2$, wherein given $H_2S$ limits have to be observed but complete removal of $CO_2$ is unnecessary.

The object is achieved by a compound of the general formula (I)

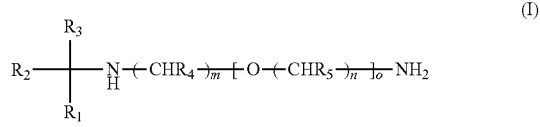

in which $R_1$, $R_2$ and $R_3$ are each independently selected from $C_{1-4}$-alkyl and $C_{1-4}$-hydroxyalkyl; $R_4$ in each repeat unit is independently selected from hydrogen, $C_{1-4}$-alkyl and $C_{1-4}$-hydroxyalkyl; $R_5$ in each repeat unit is independently selected from hydrogen, $C_{1-4}$-alkyl and $C_{1-4}$-hydroxyalkyl; m is 2, 3, 4 or 5; n is 2, 3, 4 or 5; and o is an integer from 0 to 10, especially 1 to 10. Preferably, $R_1$, $R_2$ and $R_3$ are each methyl. $R_4$ is preferably hydrogen or methyl, especially hydrogen. $R_5$ is preferably hydrogen or methyl, especially hydrogen. In a preferred embodiment, the $R_4$ or $R_5$ radical on the carbon atom bonded directly to the primary amino group is hydrogen. Preferably, m is 2, 3 or 4, especially 2 or 3, most preferably 2. Preferably, n is 2, 3 or 4, especially 2 or 3, most preferably 2. Preferably, o is 1, 2 or 3.

Suitable compounds of the formula (I) are 2-(2-tert-butylaminoethoxy)ethylamine (TBAEEA), 2-(2-(2-tert-butylaminoethoxy)ethoxy)ethylamine (TBAEEEA), 2-(tertbutylamino)ethanamine, 2-(tert-butylamino)propanamine, 2-(tertbutylamino)butanamine, 2-(2-tert-amylaminoethoxy)ethanamine, 2-(2-(1-methyl-1-ethylpropylamino)ethoxy)ethanamine, (2-(tert-butylamino)ethyl)methylamine and mixtures thereof. In a particularly preferred embodiment, the compound is 2-(2-tertbutylaminoethoxy)ethylamine (TBAEEA).

It is assumed that the primary amino group in the compound of the general formula (I) accelerates $CO_2$ absorption as a promoter through intermediate formation of a carbamate structure. The highly sterically hindered secondary amino group acts as a basicity reservoir and causes a high cyclic capacity.

The invention also relates to an absorbent for removing carbon dioxide and/or hydrogen sulfide from a fluid stream, comprising a compound of the general formula (I).

The invention also relates to the use of a compound of the general formula (I) for removing carbon dioxide and/or hydrogen sulfide from a fluid stream.

The invention also relates to a process for removing carbon dioxide and/or hydrogen sulfide from a fluid stream, in which the fluid stream is contacted with an absorbent comprising a compound of the general formula (I).

The absorbent preferably comprises an aqueous solution of a compound of the general formula (I).

In one embodiment, the absorbent comprises at least one organic solvent. The organic solvent is preferably selected from sulfolane, glycols such as ethylene glycol, diethylene glycol, ethylene glycol dimethyl ether, triethylene glycol, triethylene glycol dimethyl ether, di- or mono($C_{1-4}$-alkyl ether) monoethylene glycols and di- or mono($C_{1-4}$-alkyl ether) polyethylene glycols, N-methylpyrrolidone, N-methyl-3-morpholine, N-formylmorpholine, N-acetylmorpholine, N,N-dimethylformamide, N,N-dimethylimidazolidin-2-one, N-methylimidazole and mixtures thereof.

In particular embodiments, the absorbent comprises at least one acid. The acid is suitably selected from protic acids (Brønsted acids). The acid is selected from organic and inorganic acids. Suitable organic acids comprise, for example, phosphonic acids, sulfonic acids, carboxylic acids and amino acids. In particular embodiments, the acid is a polybasic acid.

Among the inorganic acids, preference is given to phosphoric acid and sulfuric acid.

Among the carboxylic acids, preference is given to formic acid, acetic acid, benzoic acid, succinic acid and adipic acid.

Among the sulfonic acids, preference is given to methanesulfonic acid, p-toluenesulfonic acid and 2-(4-(2-hydroxyethyl)-1-piperazinyl)ethanesulfonic acid (HEPES).

Among the phosphonic acids, preference is given to 2-hydroxyphosphonoacetic acid, 2-phosphonobutane-1,2,4-tricarboxylic acid, 1-hydroxyethane-1,1-diphosphonic acid, ethylenediaminetetra(methylenephosphonic acid), diethylenetriaminepenta(methylenephosphonic acid), bis(hexamethylene)triaminepenta(methylenephosphonic acid) (HDTMP) and nitrilotris(methylenephosphonic acid), among which 1-hydroxyethane-1,1-diphosphonic acid is particularly preferred.

In other embodiments, the absorbent is free of aminocarboxylic acids, aminosulfonic acids and phosphonic acids.

In general, the concentration of compounds of the general formula (I) in the absorbent is 10% to 60% by weight, preferably 20% to 50% by weight, more preferably 30% to 50% by weight.

The absorbent may, in addition to the compound of the general formula (I), comprise at least one tertiary amine and/or a sterically hindered primary or secondary amine.

The molar ratio of the compound of the general formula (I) to the tertiary amine and/or sterically hindered primary or secondary amines is preferably in the range from 0.05 to 1.0, more preferably in the range from 0.05 to 0.7.

A "tertiary amine" is understood to mean compounds having at least one tertiary amino group. The tertiary amine preferably comprises exclusively tertiary amino groups, meaning that it does not comprise any primary or secondary amino groups alongside at least one tertiary amino group.

The suitable tertiary amines especially include:
1. Tertiary alkanolamines such as
bis(2-hydroxyethyl)methylamine (methyldiethanolamine, MDEA), tris(2-hydroxyethyl)amine (triethanolamine, TEA), tributanolamine, 2-diethylaminoethanol (diethylethanolamine, DEEA), 2-dimethylaminoethanol (dimethylethanolamine, DMEA), 3-dimethylamino-1-propanol (N,N-dimethylpropanolamine), 3-diethylamino-1-propanol, 2-diisopropylaminoethanol (DIEA), N,N-bis(2-hydroxypropyl)methylamine (methyldiiso-propanolamine, MDIPA);
2. Tertiary amino ethers such as
3-methoxypropyldimethylamine;
3. Tertiary polyamines, for example bis-tertiary diamines such as
N,N,N',N'-tetramethylethylenediamine, N,N-diethyl-N',N'-dimethylethylenediamine, N,N,N',N'-tetraethylethylenediamine, N,N,N',N'-tetramethyl-1,3-propanediamine (TMPDA), N,N,N',N'-tetraethyl-1,3-propanediamine (TEPDA), N,N,N',N'-tetramethyl-1,6-hexanediamine, N,N-dimethyl-N',N'-diethylethylenediamine (DMDEEDA), 1-dimethylamino-2-dimethylaminoethoxyethane (bis[2-(dimethylamino)ethyl] ether), 1,4-diazabicyclo[2.2.2]octane (TEDA), tetramethyl-1,6-hexanediamine;
and mixtures thereof.

Tertiary alkanolamines, i.e. amines having at least one hydroxyalkyl group bonded to the nitrogen atom, are generally preferred. Particular preference is given to methyldiethanolamine (MDEA).

A steric hindrance is understood to mean the presence of at least one secondary or tertiary carbon atom directly adjacent to the sterically hindered position. Amines of this kind comprise, as well as sterically hindered amines, also compounds which are referred to in the prior art as highly sterically hindered amines and have a steric parameter (Taft constant) $E_s$ of more than 1.75.

A secondary carbon atom is understood to mean a carbon atom which, apart from the bond to the sterically hindered position, has two carbon-carbon bonds. A tertiary carbon atom is understood to mean a carbon atom which, apart from the bond to the sterically hindered position, has three carbon-carbon bonds. A secondary amine is understood to mean a compound having a nitrogen atom substituted by two organic radicals other than hydrogen (e.g. alkyl radical, alkenyl radical, aryl radical, alkylaryl radical, etc.).

Suitable sterically hindered primary or secondary amines are, for example, 2-(2-tert-butylaminoethoxy)ethanol (TBAEE), 2-(isopropylamino)ethanol (IPAE) and 2-amino-2-methylpropanol (2-AMP).

In other embodiments, the absorbent comprises at least one sterically unhindered primary or secondary amine. The sterically unhindered primary or secondary amine comprises, within its molecule, at least one sterically unhindered primary or secondary amino group, i.e. an amine nitrogen atom, to which only hydrogen atoms and primary carbon atoms are bonded. Sterically unhindered primary or secondary amines can accelerate $CO_2$ absorption as promoters through intermediate formation of a carbamate structure.

The sterically unhindered primary or secondary amine is, for example, selected from alkanolamines such as monoethanolamine (MEA), diethanolamine (DEA), ethylaminoethanol, 1-amino-2-methylpropan-2-ol, 2-amino-1-butanol, 2-(2-aminoethoxy)ethanol and 2-(2-aminoethoxy)ethanamine,
polyamines such as hexamethylenediamine, 1,4-diaminobutane, 1,3-diaminopropane, 3-(methylamino)propylamine (MAPA), N-(2-hydroxyethyl)ethylenediamine, 3-(dimethylamino)propylamine (DMAPA), 3-(diethylamino)propylamine, N,N'-bis(2-hydroxyethyl)ethylenediamine,
5-, 6- or 7-membered saturated heterocycles having at least one NH group in the ring, which may comprise one or two further heteroatoms selected from nitrogen and oxygen in the ring, such as piperazine, 2-methylpiperazine, N-methylpiperazine, N-ethylpiperazine, N-(2-hydroxyethyl)piperazine, N-(2-aminoethyl)piperazine, homopiperazine, piperidine and morpholine.

Particular preference is given to 5-, 6- or 7-membered saturated heterocycles having at least one NH group in the ring, which may comprise one or two further heteroatoms selected from nitrogen and oxygen in the ring. Very particular preference is given to piperazine.

The molar ratio of the compound of the general formula (I) to the sterically unhindered primary or secondary amine is preferably in the range from 1.0 to 20, more preferably in the range from 1.5 to 15.

The absorbent may also comprise additives such as corrosion inhibitors, enzymes, etc. In general, the amount of such additives is in the range from about 0.01% to 3% by weight of the absorbent.

The process or absorbent according to the invention is suitable for treatment of all kinds of fluids. Fluids are firstly gases such as natural gas, synthesis gas, coke oven gas, cracking gas, coal gasification gas, cycle gas, landfill gases and combustion gases, and secondly fluids that are essentially immiscible with the absorbent, such as liquefied petroleum gas (LPG) or liquefied natural gas (NGL, natural gas liquids). In one embodiment, the fluid stream is a flue gas stream, for example from incineration plants, production gases, synthesis gases or else ambient air. These gases arise, inter alia, in power plants, motor vehicles, production plants, ammonia production, epoxide production, cement production, the ceramics industry, coking plants, metal smelting, the steel industry, blowing agent exposure and climate-controlled working and living areas. Further $CO_2$-containing fluid streams are fermentation gases from the methanogenesis of biomasses, composting gases from the aerobic and/or anaerobic composting of biomasses, combustion gases, animal digestion gases in large-scale animal keeping and $CO_2$-containing ambient air in air conditioning in buildings and vehicles.

The fluid stream comprises carbon dioxide and/or hydrogen sulfide; it may additionally comprise further acidic gases such as COS and mercaptans. In addition, it is also possible to remove $SO_3$, $SO_2$, $CS_2$ and HCN.

The inventive compounds of the general formula (I) are of particular suitability in processes or absorbents for treatment of hydrocarbonaceous fluid streams. The hydrocarbons present are, for example, aliphatic hydrocarbons such as $C_1$-$C_4$ hydrocarbons such as methane, unsaturated hydrocarbons such as ethylene or propylene, or aromatic hydrocarbons such as benzene, toluene or xylene. More particularly, the process according to the invention is suitable for treatment of a natural gas stream. The absorbent or process according to the invention is particularly suitable for removal of $CO_2$.

In preferred embodiments, there is a partial carbon dioxide pressure in the fluid stream in the range from 0.01 to less than 3.0 bar, especially 0.03 to less than 3.0 bar. The partial pressures stated are based on the fluid stream on first contact with the absorbent in the absorption step.

The partial hydrogen sulfide pressure in the fluid stream is typically at least 2.5 mbar. In preferred embodiments, a partial hydrogen sulfide pressure of at least 0.1 bar, especially at least 1 bar, and a partial carbon dioxide pressure of at least 0.2 bar, especially at least 1 bar, is present in the fluid stream. The partial pressures stated are based on the fluid stream on first contact with the absorbent in the absorption step.

In the process according to the invention, the fluid stream is contacted with the absorbent in an absorption step in an absorber, as a result of which carbon dioxide and/or hydrogen sulfide are at least partly scrubbed out. This gives a $CO_2$- and/or $H_2S$-depleted fluid stream and a $CO_2$- and $H_2S$-laden absorbent.

The absorber used is a scrubbing apparatus used in customary gas scrubbing processes. Suitable scrubbing apparatuses are, for example, random packings, columns having structured packings and having trays, membrane contactors, radial flow scrubbers, jet scrubbers, Venturi scrubbers and rotary spray scrubbers, preferably columns having structured packings, having random packings and having trays, more preferably columns having trays and having random packings. The fluid stream is preferably treated with the absorbent in a column in countercurrent. The fluid is generally fed into the lower region and the absorbent into the upper region of the column. Installed in tray columns are sieve trays, bubble-cap trays or valve trays, over which the liquid flows. Columns having random packings can be filled with different shaped bodies. Heat and mass transfer are improved by the increase in the surface area caused by the shaped bodies, which are usually about 25 to 80 mm in size. Known examples are the Raschig ring (a hollow cylinder), Pall ring, Hiflow ring, Intalox saddle and the like. The random packings can be introduced into the column in an ordered manner, or else randomly (as a bed). Possible materials include glass, ceramic, metal and plastics. Structured packings are a further development of ordered random packings. They have a regular structure. As a result, it is possible in the case of packings to reduce pressure drops in the gas flow. There are various designs of structured packings, for example woven packings or sheet metal packings. Materials used may be metal, plastic, glass and ceramic.

The temperature of the absorption medium in the absorption step is generally about 30 to 100° C., and when a column is used is, for example, 30 to 70° C. at the top of the column and 50 to 100° C. at the bottom of the column. The total pressure in the absorption step is generally about 1 to 180 bar, preferably about 1 to 100 bar.

The process according to the invention may comprise one or more, for example two, successive absorption steps. The absorption can be conducted in a plurality of successive component steps, in which case the crude gas comprising the acidic gas constituents is contacted with a substream of the absorbent in each of the component steps. The absorbent with which the crude gas is contacted may already be partly laden with acidic gases, meaning that it may, for example, be an absorbent which has been recycled from a downstream absorption step into the first absorption step, or be partly regenerated absorbent. With regard to the performance of the two-stage absorption, reference is made to publications EP 0 159 495, EP 0 190 434, EP 0 359 991 and WO 00/00271.

The process preferably comprises a regeneration step in which the $CO_2$- and $H_2S$-laden absorbent is regenerated. In the regeneration step, $CO_2$ and $H_2S$ and optionally further acidic gas constituents are released from the $CO_2$- and $H_2S$-laden absorbent to obtain a regenerated absorbent. Preferably, the regenerated absorbent is subsequently recycled into the absorption step. In general, the regeneration step comprises at least one of the measures of heating, decompressing and stripping with an inert fluid.

The regeneration step preferably comprises heating of the absorbent laden with the acidic gas constituents. The absorbed acid gases are stripped out by means of the steam obtained by heating the solution. Rather than steam, it is also possible to use an inert fluid such as nitrogen. The absolute pressure in the desorber is normally 0.1 to 3.5 bar, preferably 1.0 to 2.5 bar. The temperature is normally 50° C. to 170° C., preferably 80° C. to 130° C., the temperature of course being dependent on the pressure.

The regeneration step may alternatively or additionally comprise a decompression. This includes at least one decompression of the laden absorbent from a high pressure as exists in the conduction of the absorption step to a lower pressure. The decompression can be accomplished, for example, by means of a throttle valve and/or a decompression turbine. Regeneration with a decompression stage is described, for example, in publications U.S. Pat. No. 4,537,753 and U.S. Pat. No. 4,553,984.

The acidic gas constituents can be released in the regeneration step, for example, in a decompression column, for example a flash vessel installed vertically or horizontally, or a countercurrent column with internals.

The regeneration column may likewise be a column having random packings, having structured packings or having trays. The regeneration column has a heater at the bottom, for example a boiler, natural circulation evaporator, forced circulation evaporator or forced circulation flash evaporator. At the top, the regeneration column has an outlet for the acid gases released. Entrained absorption medium vapors are condensed in a condenser and recirculated to the column.

It is possible to connect a plurality of decompression columns in series, in which regeneration is effected at different pressures. For example, regeneration can be effected in a preliminary decompression column at a high pressure typically about 1.5 bar above the partial pressure of the acidic gas constituents in the absorption step, and in a main decompression column at a low pressure, for example 1 to 2 bar absolute. Regeneration with two or more decompression stages is described in publications U.S. Pat. No. 4,537,753, U.S. Pat. No. 4,553,984, EP 0 159 495, EP 0 202 600, EP 0 190 434 and EP 0 121 109.

The invention is illustrated in detail by the appended drawings and the examples which follow.

Figure 1:
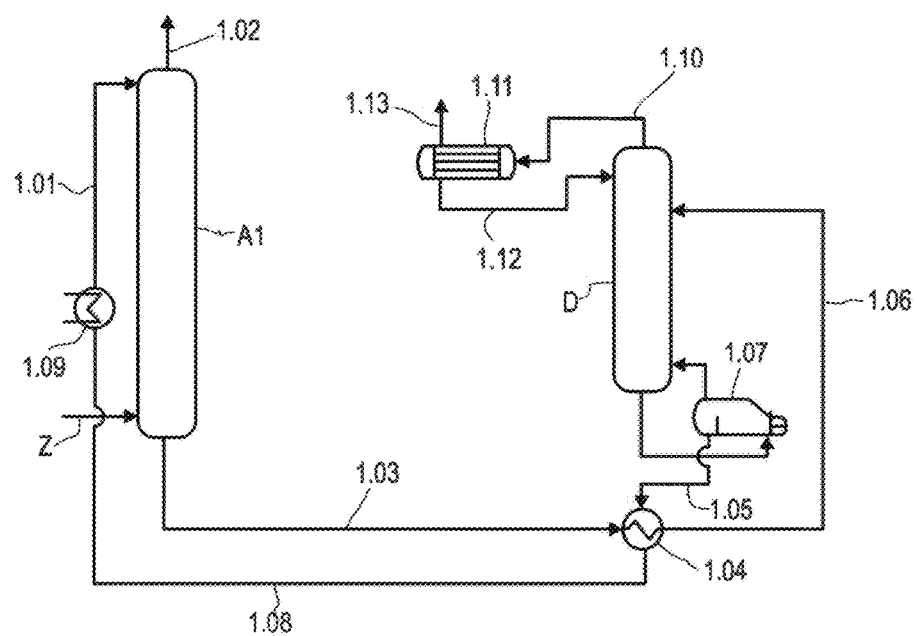
FIG. 1 is a schematic diagram of a plant suitable for performing the process according to the invention.

According to FIG. 1, via the inlet Z, a suitably pretreated gas comprising hydrogen sulfide and/or carbon dioxide is contacted in countercurrent, in an absorber A1, with regenerated absorbent which is fed in via the absorbent line 1.01. The absorbent removes hydrogen sulfide and/or carbon dioxide from the gas by absorption; this affords a hydrogen sulfide- and/or carbon dioxide-depleted clean gas via the offgas line 1.02.

Via the absorbent line 1.03, the heat exchanger 1.04 in which the $CO_2$- and/or $H_2S$-laden absorbent is heated up with the heat from the regenerated absorbent conducted through the absorbent line 1.05, and the absorbent line 1.06, the $CO_2$- and/or $H_2S$-laden absorbent is fed to the desorption column D and regenerated. From the lower part of the desorption column D, the absorbent is conducted into the boiler 1.07, where it is heated. The mainly water-containing vapor is recycled into the desorption column D, while the regenerated absorbent is fed back to the absorber A1 via the absorbent line 1.05, the heat exchanger 1.04 in which the regenerated absorbent heats up the $CO_2$- and/or $H_2S$-laden absorbent and at the same time cools down itself, the absorbent line 1.08, the cooler 1.09 and the absorbent line 1.01. Instead of the boiler shown, it is also possible to use other heat exchanger types to generate the stripping vapor, such as a natural circulation evaporator, forced circulation evaporator or forced circulation flash evaporator. In the case of these evaporator types, a mixed-phase stream of the regenerated absorbent and stripping vapor is returned to the bottom of the desorption column, where the phase separation between the vapor and the absorbent takes place. The regenerated absorbent to the heat exchanger 1.04 is either drawn off from the circulation stream from the bottom of the desorption column to the evaporator or conducted via a separate line directly from the bottom of the desorption column to the heat exchanger 1.04.

The $CO_2$- and/or $H_2S$-containing gas released in the desorption column D leaves the desorption column D via the offgas line 1.10. It is conducted into a condenser with integrated phase separation 1.11, where it is separated from entrained absorbent vapor. Condensation and phase separation also present separately from one another. Subsequently, a liquid consisting mainly of water is conducted through the absorbent line 1.12 into the upper region of the desorption column D, and a $CO_2$- and/or $H_2S$-containing gas is discharged via the gas line 1.13.

Figure 2:
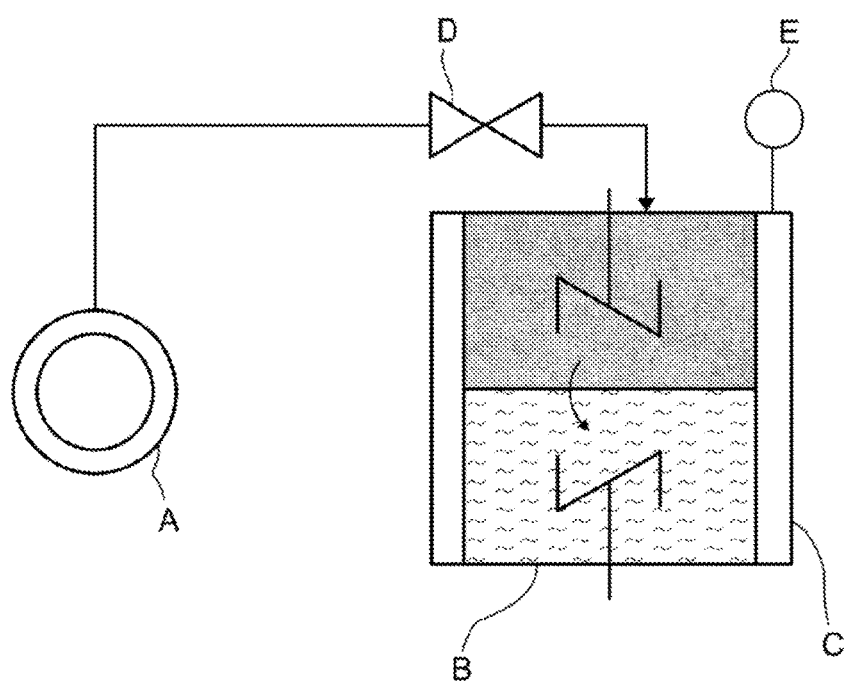
FIG. 2 is a schematic diagram of a twin stirred cell arrangement used to determine the relative $CO_2$ absorption rates of absorbents.

In FIG. 2, the following reference symbols are used: A=$CO_2$ storage vessel, B=twin stirred cell, C=temperature regulator, D=metering valve, E=manometer. According to FIG. 2, a liquid phase of the absorbent to be tested s present in the lower part of the twin stirred cell B, and is in contact with the gas phase above it via a phase boundary. The liquid and gas phase can each be mixed with a stirrer. The twin stirred cell B is connected to the $CO_2$ storage vessel A via a metering valve D. The pressure that exists in the twin stirred cell B can be determined by means of the manometer E. In the measurement, the volume flow rate of carbon dioxide is recorded, the volume flow rate being adjusted such that a constant pressure exists in twin stirred cell B.

EXAMPLES

The following abbreviations are used:
TSC: twin stirred cell
HPCy$_2$: dicyclohexylphosphine
MDEA: methyldiethanolamine
MeOH: methanol
MTBE: methyl tert-butyl ether
TBAEE: 2-(2-tert-butylaminoethoxy)ethanol
TBAEEA: 2-(2-tert-butylaminoethoxy)ethylamine
THF: tetrahydrofuran Example 1

Synthesis of 2-(2-tert-butylaminoethoxy)ethylamine (TBAEEA)

A) Synthesis of Catalyst Complex A

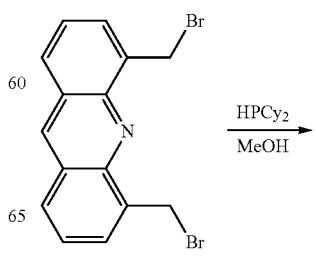

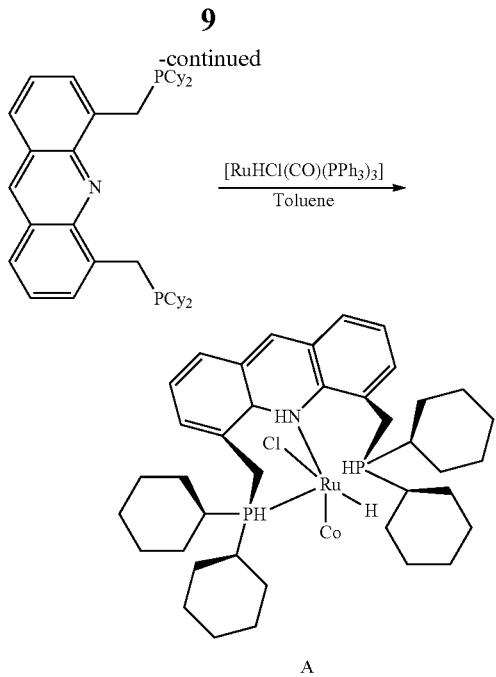

A

A1) Synthesis of 4,5-bis(dicyclohexylphosphinomethyl)acridine

A solution of 4,5-bis(bromomethyl)acridine (5.2 g, 14.2 mmol) and dicyclohexylphosphine (8.18 g, 36.8 mmol) in 65 mL of anhydrous degassed methanol was heated to 50° C. under an argon atmosphere for 66 h. After cooling to room temperature, triethylamine (5.72 g, 56.7 mmol) was added and the mixture was stirred for 1 h. Evaporating the solvent gave a yellow-white solid in red oil. Extraction by means of 3×40 mL of methyl tert-butyl ether (MTBE) and concentration of the filtrate gave a red-brown oil ($^1$H NMR: mixture of product and HPCy$_2$). The oil was taken up in a little warm MTBE and ice-cooled methanol was added, which caused the precipitation of a yellow microcrystalline solid. Isolation and drying under reduced pressure gave air-sensitive 4,5-bis(dicyclohexylphosphinomethyl)acridine (2.74 g, 33%) as a yellow powder.

A2) Synthesis of Catalyst Complex A 4,5-Bis(dicyclohexylphosphinomethyl)acridine (1855 mg, 3.1 mmol) and [RuHCl(CO)(PPh$_3$)$_3$]$^2$ (2678 mg, 2.81 mmol) were heated to 70° C. in 80 mL of degassed toluene for 2 h. The resulting dark brown solution was concentrated to dryness, and the residue was suspended in 3×20 mL of hexane and isolated by filtration. Drying under reduced pressure gave catalyst complex A (1603 mg, 75%) as an orange-brown powder.

B) Synthesis of 2-(2-tert-butylaminoethoxy)ethylamine (TBAEEA)

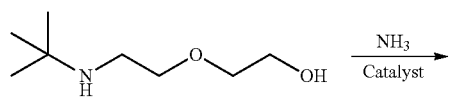

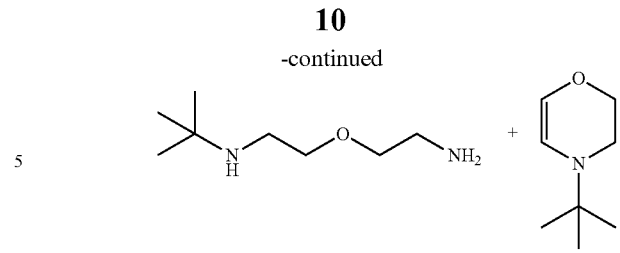

Catalyst complex A (38.3 mg), THF (50 mL) and tert-butylaminoethoxyethanol were initially charged under an argon atmosphere in a 160 mL Parr autoclave (V4A stainless steel) with a magnetically coupled pitched blade stirrer (stirrer speed: 200-500 revolutions/minute). Ammonia (20.5 g) was precondensed at room temperature and metered in. The steel autoclave was heated electrically to 180° C. and heated (internal temperature measurement) while stirring (500 revolutions/minute) for 24 h. After heating the reaction mixture in the autoclave to 180° C., an autogenous pressure of 89 bar was evolved. After cooling to room temperature, decompression of the autoclave and outgassing of the ammonia at standard pressure, the reaction mixture was analyzed by means of GC ("Rtx®-5 Amine" column, length 30 m, internal diameter 0.32 mm, d$_f$ 1.5 µm, 60° C.-4° C./min-280° C.). At quantitative conversion, 90% of the desired 2-(2-tertbutylaminoethoxy)ethylamine are formed according to GC area % evaluation. The main by-product at 6% is the cyclized morpholine derivative depicted. The product was purified by distillation (distillation temperature 70° C. at 0.5 mbar).

Example 2

Figure 3:
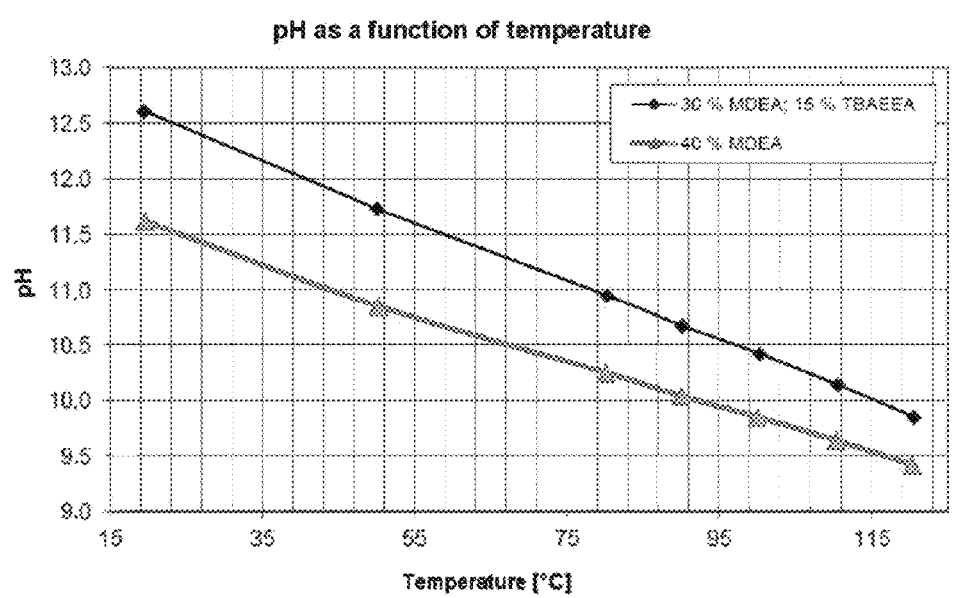
FIG. 3 shows the pH of aqueous solutions of MDEA and MDEA+TBAEEA as a function of temperature.

For mixtures consisting of 40% by weight of MDEA and 60% by weight of water (2-1) and 30% by weight of MDEA, 15% by weight of TBAEEA and 55% by weight of water (2-2), the temperature dependence of the pH was determined. A pressure apparatus was used, in which the pH can be measured up to 120° C. The results are shown in FIG. 3. The mixture comprising TBAEEA (2-2) shows a much higher pH at 20° C. than the mixture comprising MDEA (2-1). The pH is a measure of how well CO$_2$ or H$_2$S can be bound. The higher the pH of the solution, the more CO$_2$ or else H$_2$S can be bound. In other words, at low temperatures as typically exist in absorbers, a high pH is advantageous. Overall, the mixture of TBAEEA+MDEA (2-2) shows a greater temperature dependence than the reference example comprising MDEA (2-1). For the solution (2-2) comprising TBAEEA and MDEA, the gradient is −0.027 pH unit/K, but for the MDEA solution (2-1) only −0.022 pH unit/K. For the regeneration, a maximum pH differential between higher and lower temperatures is advantageous, since the acidic components absorbed are released again with lower energy expenditure at higher temperatures and correspondingly lower pH values.

Example 3

In a twin stirred cell (TSC) according to FIG. 2, the relative CO$_2$ absorption rates of aqueous absorbents were measured.

The twin stirred cell had an internal diameter of 85 mm and a volume of 509 mL. The temperature of the cell was kept at 40° C. during the measurements. In order to mix the gas and liquid phases, the cell according to FIG. 2 comprised two stirrers. Before commencement of the measurement, the twin stirred cell was evacuated. A defined volume of degassed absorbent was added to the twin stirred cell and the temperature was regulated at 40° C. The stirrers were already switched on during the heating of the unladen absorbent. The stirrer speed was selected such that a planar phase boundary formed between the liquid phase and the gas phase. Development of waves at the phase interface has to be avoided since there would otherwise be no defined phase interface. After the desired experimental temperature had been attained, carbon dioxide was introduced into the reactor by means of a metering valve. The volume flow rate was controlled such that the pressure was constant at 100 mbar abs over the entire experiment. With increasing experimental duration, the volume flow rate decreased since the absorption medium became saturated over time and the absorption rate decreased. The volume flow rate was recorded over the entire period. At the start of the experiment, the flow rates carbon dioxide flow rate was about 4 L (STP)/h. The experiment was ended as soon as the carbon dioxide flow rate was less than 0.02 L (STP)/h. The absorption medium was in an equilibrium state at the end of the experiment.

The following absorbents were used:
3-1) aqueous solution of MDEA (41% by weight)
3-2) aqueous solution of MDEA (30% by weight)+TBAEE (15% by weight)
3-3) aqueous solution of MDEA (30% by weight)+TBAEEA (15% by weight)

The absorption rate was determined at 20% and 50% of the loading attained at the end of the experiment (EQM). The values were normalized to the absorption rate of absorbent 3-1 at 20% and 50% EQM. The results are reported in the following table:

| Example | System | Relative absorption rate at 20% EQM** | Relative absorption rate at 50% EQM** |
|---|---|---|---|
| 3-1* | MDEA (41% by wt.) | 100% | 100% |
| 3-2* | MDEA (30% by wt.) + TBAEE (15% by wt.) | 136% | 128% |
| 3-3 | MDEA (30% by wt.) + TBAEEA (15% by wt.) | 355% | 309% |

*comparative example
**based on example 3-1

It can be seen that, in inventive example 3-3, the absorption rate is much higher than in comparative examples 3-1 and 3-2, irrespective of the particular $CO_2$ loading.

Example 4

To estimate the cyclic capacity, a loading experiment and a subsequent stripping experiment were conducted for the following aqueous absorbents:
4-1) 30% by wt. of MDEA+8% by wt. of piperazine
4-2) 30% by wt. of MDEA+15% by wt. of TBAEE
4-3) 30% by wt. of MDEA+15% by wt. of TBAEEA The apparatus used was a thermostated glass cylinder with a reflux condenser connected above. The reflux condenser was operated at a temperature of about 5° C. and prevented water and amine from being discharged during the loading and stripping.

At 40° C., 100 mL of the absorbent were introduced into the glass cylinder. Through a frit at the lower end of the glass cylinder, 8 L (STP)/h of pure $CO_2$ were bubbled into the absorption solution for about 4 h. At the end of the experiment, the loading of $CO_2$ in the absorbent was determined by means of measurement of the total inorganic carbon content (TIC).

Figure 4:
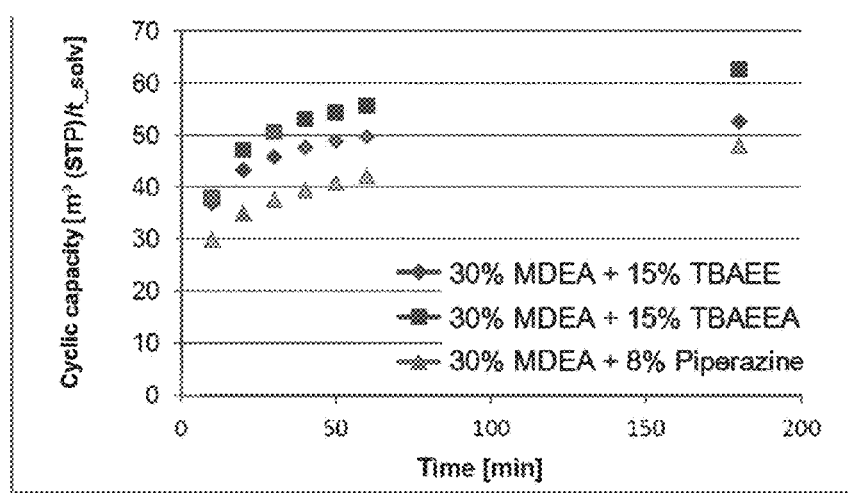
FIG. 4 shows the cyclic capacity of aqueous MDEA solutions comprising piperazine, TBAEE and TBAEEA.

The laden solutions were stripped with nitrogen (8 L (STP)/h) at 80° C. in an apparatus of identical construction. Over the course of 60 min, samples of the absorbent were taken every 10 min and analyzed for the $CO_2$ content. The stripping experiments were continued for a further 2 h, and finally the loading of $CO_2$ in the absorbent was determined (total stripping time: 180 min). The difference between the $CO_2$ loading attained at the end of the loading experiment and the $CO_2$ loading determined as a function of stripping time are used to calculate the cyclic capacities of the three absorbents. The results are shown in FIG. 4. It is found that the mixture comprising TBAEEA (4-3) has the highest cyclic capacity, irrespective of the stripping time.

Example 5

The volatility of the following absorbents was determined:
5-1) 41% by wt. of MDEA
5-2) 30% by wt. of MDEA+15% by wt of TBAEE
5-3) 30% by wt. of MDEA+15% by wt of TBAEEA A minimum volatility is advantageous in order to ensure a minimum discharge of amines together with the cleaned gas or together with the removed acid gas from the absorption plant.

An apparatus as per the loading and stripping apparatus described in example 4 was used. The glass cylinder was heated to and kept at a temperature of 50° C., and 100 mL of the absorbent were introduced in each case. Through a frit at the lower end of the glass cylinder, 20 L (STP)/h of pure $CO_2$ were bubbled into the absorption solution for about 8 h. In contrast to example 4, the liquids condensed out were not passed back into the glass cylinder but collected separately and analyzed for their composition after the end of the experiment. The results are shown in the following table:

| | | Amount | Condensate composition | | | |
|---|---|---|---|---|---|---|
| Example | System | of condensate [g] | Water [g/ 100 g] | MDEA [g/ 100 g] | TBAEE [g/ 100 g] | TBAEEA [g/ 100 g] |
| 5-1* | MDEA | 15.811 | 99.1 | 0.37 | — | — |
| 5-2* | MDEA + TBAEE | 17.284 | 99.2 | 0.39 | 0.37 | — |
| 5-3 | MDEA + TBAEEA | 16.949 | 99.2 | 0.42 | — | 0.27 |

*comparative example

It can be seen that, in example 5-3, the volatility of the inventive compound TBAEEA is much lower than that of the compounds in comparative examples 5-1 and 5-2.

The invention claimed is:
1. An absorbent for removing carbon dioxide and/or hydrogen sulfide from fluid streams, comprising an aqueous solution of a compound of the general formula (I)

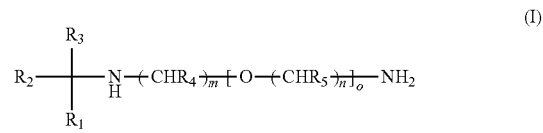

in which $R_1$ and $R_3$ are each independently selected from $C_{1-4}$-alkyl and $C_{1-4}$-hydroxyalkyl;

each $R_4$ is independently selected from hydrogen, $C_{1-4}$-alkyl and $C_{1-4}$-hydroxyalkyl;

each $R_5$ is independently selected from hydrogen, $C_{1-4}$-alkyl and $C_{1-4}$-hydroxyalkyl;

m is 2, 3, 4 or 5;

n is 2, 3, 4 or 5; and o is an integer from 1 to 10.

2. The absorbent according to claim 1, with the proviso that the $R_5$ radical on the carbon atom bonded directly to the primary amino group is hydrogen.

3. The absorbent according to claim 1, wherein the absorbent comprises at least one organic solvent.

4. The absorbent according to claim 1, wherein the absorbent comprises at least one acid.

5. The absorbent according to claim 1, wherein the concentration of the compound of the formula (I) in the absorbent is 10% to 60% by weight.

6. The absorbent according to claim 1, also comprising at least one tertiary amine and/or a sterically hindered primary or secondary amine.

7. The absorbent according to claim 6, wherein the tertiary amine is methyldiethanolamine.

8. A process for removing carbon dioxide and/or hydrogen sulfide from fluid streams, the process comprising:
contacting an absorbent according to claim 1 with a fluid stream, to obtain a $CO_2$- and $H_2S$-depleted fluid stream and a $CO_2$- and $H_2S$-laden absorbent.

9. The process according to claim 8, wherein the fluid stream comprises at least one hydrocarbon.

10. The process according to claim 8, wherein the fluid stream has a total pressure of at least 3.0 bar.

11. The process according to claim 8,
further comprising: regenerating the $CO_2$- and $H_2S$-laden absorbent,
wherein said regenerating comprises at least one of heating, decompressing and stripping the absorbent with an inert fluid.

12. A compound of the general formula (Ia)

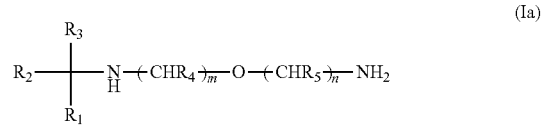

(Ia)

in which $R_1$, $R_2$ and $R_3$ are each independently selected from $C_{1-4}$-alkyl and $C_{1-4}$-hydroxyalkyl;

each $R_4$ is independently selected from hydrogen, $C_{1-4}$-alkyl and $C_{1-4}$-hydroxyalkyl;

each $R_5$ is independently selected from hydrogen, $C_{1-4}$-alkyl and $C_{1-4}$-hydroxyalkyl; and m is 2, 3, 4 or 5.

13. The compound according to claim 12, with the proviso that the $R_5$ radical on the carbon atom bonded directly to the primary amino group is hydrogen.

14. The compound according to claim 13, which is 2-(2-tert-butylaminoethoxy)ethylamine.

* * * * *

UNITED STATES PATENT AND TRADEMARK OFFICE
CERTIFICATE OF CORRECTION

PATENT NO. : 10,214,482 B2
APPLICATION NO. : 15/506472
DATED : February 26, 2019
INVENTOR(S) : Thomas Ingram et al.

Page 1 of 1

It is certified that error appears in the above-identified patent and that said Letters Patent is hereby corrected as shown below:

In the Specification

In Column 8, Line 28 (approx.), "tested s" should read -- tested is --, therefor.

In the Claims

In Column 13, Line 1, Claim 1, "$R_1$ and $R_3$" should read -- $R_1$, $R_2$ and $R_3$ --, therefor.

In Column 14, Lines 10-17 (approx.), Claim 12, " $CHR_5\!\!\!-\!\!\!\!\!\underset{n}{\phantom{x}}$ " should read --  --, therefor.

Signed and Sealed this
Fifth Day of May, 2020

Andrei Iancu
*Director of the United States Patent and Trademark Office*